(12) United States Patent
Ladebeck

(10) Patent No.: US 7,923,691 B2
(45) Date of Patent: Apr. 12, 2011

(54) METHOD FOR PRODUCING AN ATTENUATION MAP

(75) Inventor: Ralf Ladebeck, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 113 days.

(21) Appl. No.: 12/453,329

(22) Filed: May 7, 2009

(65) Prior Publication Data

US 2009/0278049 A1    Nov. 12, 2009

(30) Foreign Application Priority Data

May 8, 2008    (DE) .......................... 10 2008 022 816

(51) Int. Cl.
*G01T 1/166* (2006.01)
(52) U.S. Cl. .................................. 250/363.04
(58) Field of Classification Search ............ 250/363.04; 378/4; 600/407, 422
See application file for complete search history.

(56) References Cited

U.S. PATENT DOCUMENTS

2009/0105583 A1 * 4/2009 Martin et al. ................. 600/422

FOREIGN PATENT DOCUMENTS

DE     102006033383 A1    1/2008
WO     WO 9736189 A1     10/1997

* cited by examiner

*Primary Examiner* — David P Porta
*Assistant Examiner* — Mark R Gaworecki
(74) *Attorney, Agent, or Firm* — Harness, Dickey & Pierce, P.L.C.

(57) ABSTRACT

A method is disclosed for producing an attenuation map for a component of an MR/PET system. In at least one embodiment, the method includes ascertaining attenuation values of the component, producing a basic map from the attenuation values, ascertaining a position of the component relative to an examination volume of the MR/PET system, and producing the attenuation map by correcting the basic map using the ascertained position. This enables the actual position of the components to be taken into account in the attenuation correction.

10 Claims, 3 Drawing Sheets

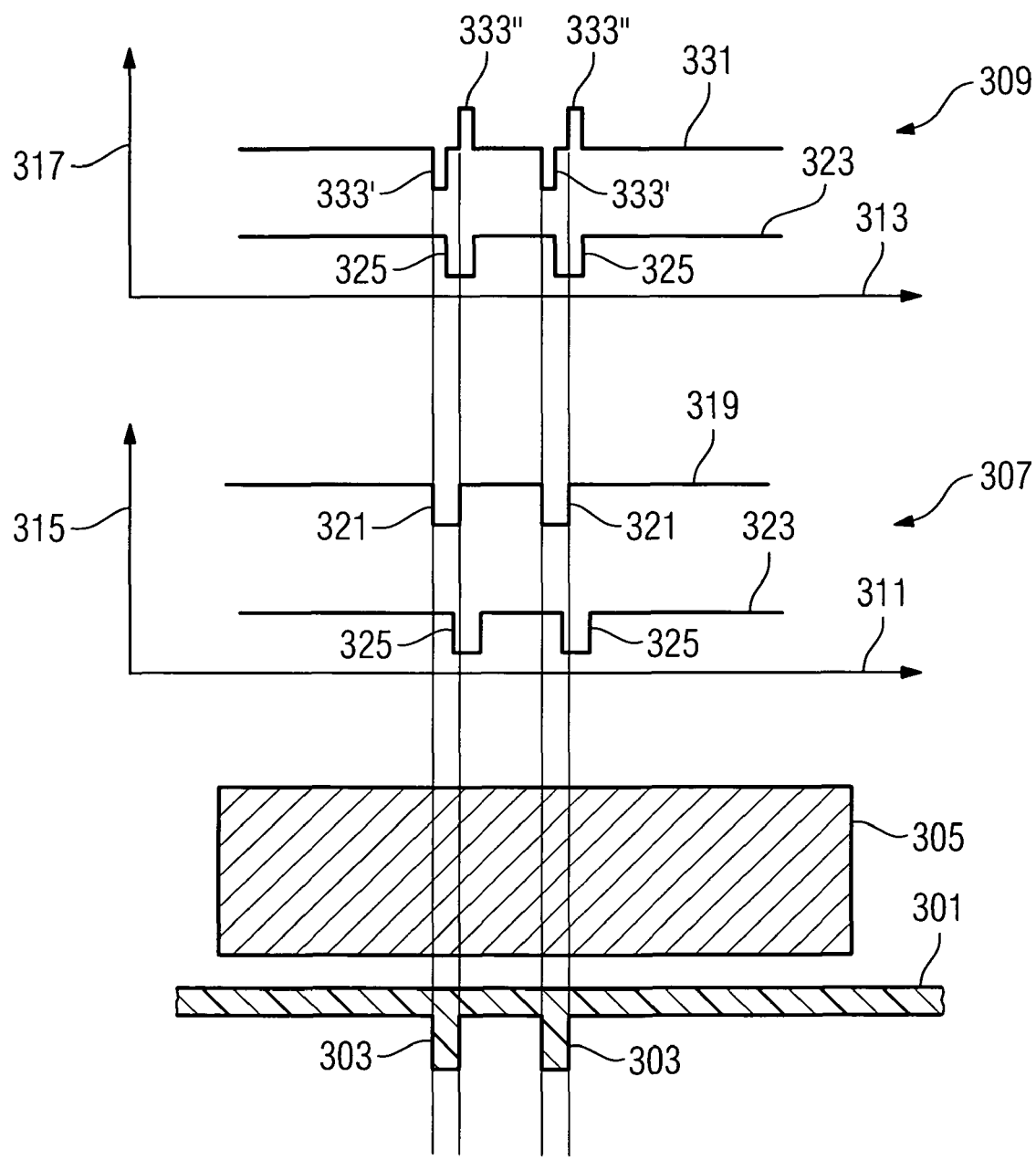

ID OF AN
ATTENUATION MAP

PRIORITY STATEMENT

The present application hereby claims priority under 35 U.S.C. §119 on German patent application number DE 10 2008 022 816.8 filed May 8, 2008, the entire contents of which is hereby incorporated herein by reference.

FIELD

At least one embodiment of the present invention generally relates to a method for producing an attenuation map for a component of an MR/PET system.

BACKGROUND

In addition to magnetic resonance tomography (MR), increasingly widespread use in medical diagnostics has in recent years also been made of positron emission tomography (PET). While MR is an imaging method for showing internal structures of the body and displaying sectional views thereof, PET enables metabolic activities to be visualized and quantified in vivo.

PET exploits the particular characteristics of positron emitters and of positron annihilation to quantitatively determine the functioning of organs or cell regions. Appropriate radiopharmaceuticals that are marked with radionuclides are therein administered to the patient prior to the examination. As they decay the radionuclides emit positrons which after a short distance interact with an electron, as a result of which what is termed an annihilation occurs. This gives rise to two gamma quanta which fly apart in opposite directions (displaced by 180°). The gamma quanta are registered within a specific time window by two PET detector modules located mutually opposite (coincidence measurement), as a result of which the site of the annihilation is determined at a position on the connecting line between said two detector modules.

For detection purposes the detector module must in the case of PET generally cover much of the length of the gantry arc. The module is subdivided into detector elements having a lateral length of a few millimeters. Upon detecting a gamma quantum each detector element generates an event record indicating the time and the detection site, which is to say the relevant detector element. This information is conveyed to a high-speed logic array and compared. A gamma decay process on the connecting line between the two associated detector elements is assumed if two events coincide within a maximum time span. The PET image is reconstructed using a tomography algorithm, what is termed back-projection.

It is known to employ combined PET/CT devices for, for example, compensating the deficient spatial resolution of PET systems. CT simultaneously offers a representation of the patient's anatomy so that when the CT and PET data are mutually superimposed it is possible to establish precisely where in the body the PET activity occurred. In combined PET/CT devices a PET device and CT device are typically arranged one behind the other such that the patient can be transferred seamlessly from one device to the other during an examination. The two measurements can then be performed in direct succession.

It is advantageous to combine a PET device with an MR device because MR offers a higher soft tissue contrast than CT. Combined MR/PET systems are already known in which the PET detectors are arranged within an opening defined by the MR magnet together with the gradient system and exciting coil. They are therein positioned next to the exciting coil so that the examination volumes of the MR and PET system do not coincide but are offset in the z direction. Analogously to the PET/CT system it is consequently not possible here to measure PET and MR data simultaneously.

In this case it is particularly preferred for the PET device to be arranged inside the MR device and for the two examination volumes to be mutually superimposed. It will then be possible to ascertain both morphological MR data and PET data during a single measuring operation. Apart from the time-saving impact, both image data sets can be presented in a simple manner, mutually superimposed so that a diagnosis will be made easier for the physician.

For integrating the PET device and MR device it is necessary to arrange the PET detectors inside the MR device so that the imaging volumes will be positioned isocentrically. For example, the PET detectors can be arranged on a support structure (support tube, gantry) located inside the MR device. They can include, for example, 60 detectors arranged annularly on the support tube. Each of the detectors, which can also be combined into detector blocks, requires a connected cooling means and electric supply lines. These must likewise be arranged inside the MR device. A number of signal processing units are additionally required that are likewise arranged inside the MR device. These are connected to the detectors via the electric supply lines and serve for signal processing.

When, though, MR and PET are used jointly in a combined system, the gamma quanta will be attenuated by anything situated between the site of origin of the respective gamma quanta and the PET detector. The attenuation must be taken into account in the reconstruction of PET images so that image artifacts will be avoided. Situated between the site of origin of the gamma quantum in the patient's body and the acting PET detector are tissue within the patient's body as well as air, generally, and a part of the MR/PET system itself, for example a cover of the patient opening or a patient positioning table. The attenuation values of the components or accessory parts requiring to be taken into account are compiled into attenuation maps (µ maps). Thus, for example, an attenuation map can be produced for the patient positioning table. The same applies to, for instance, local coils attached to the patient for MR examinations. In order to produce the attenuation map it is necessary to ascertain and combine the attenuation values. They can be ascertained by means of, for example, a CT recording or PET transmission measurement of the respective component. Attenuation maps of said kind can be measured on a once-only basis because the attenuation values do not change over the life of the respective component.

It is known in the case of PET/CT systems to calculate an attenuation map from CT recordings using the x-ray absorption coefficients and use it to correct the attenuation of PET data. This can also be employed in measuring attenuation values of the components. It is not possible in the case of PET systems to directly ascertain the attenuation map from the actual measurement data. Homogeneous PET phantoms have to be used for measuring so that the intensity of the gamma quanta arising will be known.

SUMMARY

In at least one embodiment of the present invention a method is disclosed for producing an attenuation map for a component of an MR/PET system.

According to one embodiment variant of the invention, a method for producing an attenuation map for a component of an MR/PET system is disclosed that comprises the following method-specific steps:
Ascertaining attenuation values of the component,
producing a basic map from the attenuation values,
ascertaining a position of the component relative to an examination volume of the MR/PET system, and
producing the attenuation map by correcting the basic map using the ascertained position.

The position of the respective component affects the attenuation of the gamma quanta. Thus, for example, the patient positioning table will generally not be homogeneous in structure over its entire surface area. It will have, for instance, stabilizing cross-braces. The structure will also be reflected in the corresponding attenuation map in which the attenuation values of each point on the patient positioning table are stored in accordance with the material present there and the material's thickness. The actual position of the respective component within the examination volume during the examinations therefore has to be taken into account when the attenuation map is being applied in the reconstruction of the respective PET image. In the case of the exemplary patient positioning table it will thus be relevant which part thereof is situated at the time between the site of origin of the gamma quanta and the relevant PET detector because that will substantially affect the attenuation. A reference can be established here to the origin of the MR/PET device's coordinate system, which origin is located, for example, in the center of the examination volume. The examination volume of the PET part would have to be taken here as a basis if the examination volumes of the MR and PET part did not coincide.

In principle, an attenuation map for the relevant components can be measured on a once-only basis for a model series of an MR/PET system having virtually identical components from one specimen to the next and used in reconstructing PET images. It is, however, necessary to take account of any manufacturing tolerances occurring during the assembly of individual specimens of the MR/PET systems. Thus, for example, the patient positioning table can have different positions in the transverse direction. Here it is necessary to determine the position of the patient positioning table when each individual MR/PET system is being calibrated and accordingly match the attenuation map to the actual position. The position cannot be expected to change from measurement to measurement so that a one-time calibration will suffice. It is, though, possible here to recalibrate after certain periods of time. The same applies to other permanently installed components such as, for example, a head coil or neck coil that are connected to the patient positioning table. The position in the z direction of the patient positioning table and the components connected thereto is known very precisely because the patient is also positioned via that within the examination volume. This position can therefore be made available accordingly for each measurement and reconstruction of the PET images.

Attenuation maps must basically likewise be ascertained and taken into account for local coils. The position of the local coils is, though, different for each measurement so that requirements differing from those applying to static components here have to be placed on ascertaining the position. One-off measurements in calibrating the MR/PET system are out of the question.

The position of the attenuating components must be known approximately with a tolerance amounting to half a PET pixel, which is approximately 2 mm. Registering the position of the patient positioning table with this degree of accuracy would require a complex measuring mechanism.

The attenuation values of the component under consideration can be ascertained using known methods by way of PET or CT measurements. Producing the basic map means assembling the component's attenuation values. If the component's position relative to an examination volume of the MR/PET system is then ascertained, the attenuation map can be produced by correcting the basic map using the ascertained position. This will allow, for example, assembly tolerances to be taken into account in the reconstruction of the PET images.

What is advantageous is an embodiment of the invention of a kind such that the component has marking elements embodied as able to emit a magnetic resonance signal after being excited and that the component's position is ascertained by recording an MR image and evaluating image data contained about the markings. The marking elements can be, for example, cross-shaped containers that are filled with water or another MR-active material and attached to the component. From the position of the cross it is possible in the MR image to ascertain the component's position relative to the examination volume and produce the attenuation map. This embodiment of the invention is suitable for both permanently installed components (patient positioning table, head coil, etc.) and variably positionable components (local coils, positioning aids, etc.)

In an advantageous embodiment of the invention, ascertaining the position of the component comprises the following method-specific steps:
Combining the component with a homogeneous MR phantom,
recording an MR data set of the MR phantom, and
evaluating the MR data set in terms of the component's position compared with the examination volume.

Using the MR phantom here enables permanently installed components to be calibrated once only. What is particularly advantageous therein is that the component's position can be determined in a simple manner outside the MR/PET system's actual measuring mode, meaning that little measuring time needs to be made available.

It is likewise possible to combine the two example embodiments so that permanently installed components will be taken into account once only in the calibration of the MR/PET system, while variably positionable components will have been furnished with the MR-active marking elements and so be taken into consideration during the respective MR measurement.

What is advantageous is an embodiment of the invention of a kind such that the MR/PET system includes an optical registration system and the position of the component is ascertained by registering it by means of the registration system. Already known 3D scanners, for example, are suitable for said kind of registering of the component's position. What is therein advantageous is registering the position of the components in realtime independently of the MR/PET system. This makes it possible, for example, to take account of components that are in motion during measuring. This is important, for example, in the case of local coils that are situated on the chest and move during measuring due to the patient's breathing.

What is advantageous is an embodiment of the invention of a kind such that ascertaining the position of the component comprises the following method-specific steps:
Combining the component with a homogeneous PET phantom,
measuring a PET data set of the PET phantom,
reconstructing a PET image from the PET data set, and
evaluating the PET image in terms of the component's position compared with the examination volume.

A calibration for permanently connected components such as the patient positioning table or head coil is possible here with little additional overhead.

It is advantageous for the PET image to be reconstructed without taking attenuation values into account and for the evaluation of the PET image to comprise the following method-specific steps:

Ascertaining location-dependent intensity modulations in the PET image, evaluating the location of the intensity modulations in terms of the location of the examination volume, and establishing the component's position using the location of the intensity modulations.

What is herein exploited is that the structure of the component will be reflected in the PET image when it is reconstructed without taking attenuation values into account. To that extent an initial indication enabling the attenuation map to be corrected will here be provided for the position of the component within the examination volume.

In the case particularly of regularly structured components such as, for example, the patient positioning table, intensity modulations occur in the PET image from the location of which modulations the component's position can be ascertained. The intensity modulations do not therein have to be regular.

In an advantageous embodiment of the invention the PET image is reconstructed using the basic map and a predefined position of the component, and evaluating of the PET image comprises the following method-specific steps:

Examining the PET image for position artifacts, correcting the component's position taking identified position artifacts into account, reconstructing another PET image using the basic map at the component's corrected position, and iterating the last three method-specific steps until no more position artifacts can be detected.

In this embodiment variant of the invention, the PET image of the PET phantom is reconstructed using the basic map and a predefined position of the component. In the example of the patient positioning table it could be assumed that its starting position is in the center of the MR/PET system. In this case position artifacts would occur in the PET image if the patient positioning table is not positioned centrally. If the patient positioning table has been displaced in the transverse direction, then the attenuation will be over- or undercompensated in the profile if there are changes in the thickness of the patient positioning table. Minima or maxima would consequently occur at corresponding locations as position artifacts in the intensity profile. The component's position must be corrected accordingly and taken into account when the PET image is reconstructed again. This PET image is again examined for the occurrence of position artifacts and, if necessary, the position of the component will be corrected again. This process keeps being repeated until no further position artifacts occur. In that case the component's position will have been determined, so the definitive attenuation map can be produced.

BRIEF DESCRIPTION OF THE DRAWINGS

Further advantages and embodiments of the invention will emerge in the example embodiments described below in association with the figures, in which:

FIG. 4 is a schematic juxtaposition of two embodiment variants of the invention.

DETAILED DESCRIPTION OF THE EXAMPLE EMBODIMENTS

Figure 1:
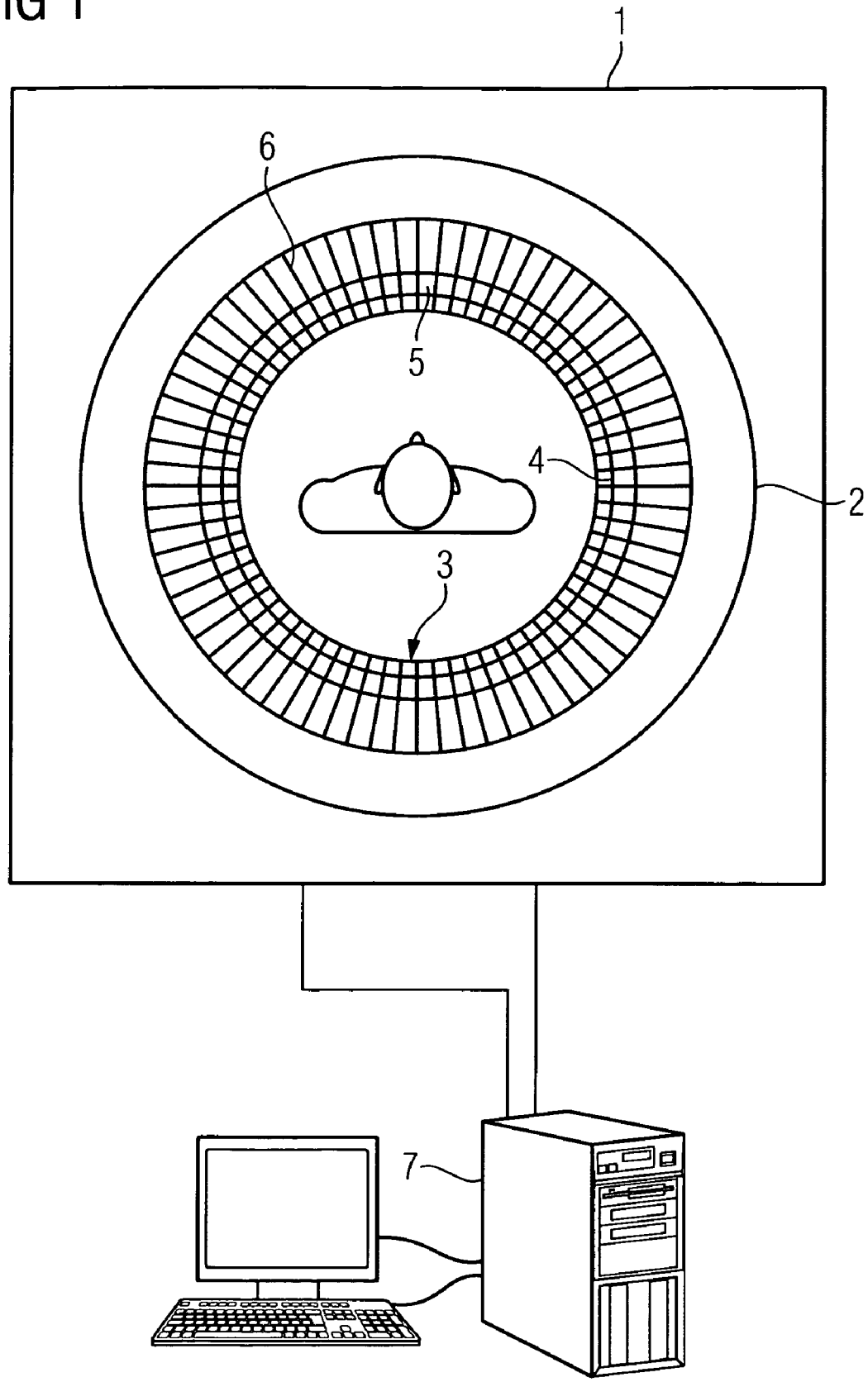
FIG. 1 shows a known embodiment of an MR/PET device.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention can be used preferably on a combined MR/PET device. A combined device has the advantage that both MR and PET data can be obtained isocentrically. This enables the examination volume within the region of interest to be precisely defined using the data of the first modality (PET) and this information to be used in the other modality (e.g. magnetic resonance). Although it is possible to transfer the volume information relating to the region of interest from an external PET device to an MR device, increased overhead will be required for registering the data. All data able to be determined by means of magnetic resonance or other imaging methods can in general be ascertained in the region of interest selected on the PET data set. Instead of the spectroscopy data it is also possible, for example, to obtain fMR data, diffusion maps, T1- or T2-weighted images, or quantitative parameter maps by means of magnetic resonance examinations in the region of interest. Computed tomography methods (e.g. perfusion measurement, multiple-energy imaging) or x-raying can likewise be employed. What is advantageous about the described method is in each case that the region of interest can be narrowed down very selectively by means of the PET data set to a specifically present patient pathology.

It is, though, additionally possible by using a plurality of what are termed tracers to show various biological characteristics in the PET data set and thus yet further optimize the region of interest and the volume established thereby, or to at once select a plurality of different examination volumes that will then be analyzed in succeeding examinations.

FIG. 1 shows a known device 1 for representing MT and PET images in mutually superimposed form. The device 1 consists of a known MR tube 2. The MR tube 2 defines a longitudinal direction z extending orthogonally to the drawing plane of FIG. 1.

As shown in FIG. 1, located coaxially inside the MR tube 2 are a plurality of PET detection units 3 arranged mutually opposite in pairs around the longitudinal direction z. The PET detection units 3 consist preferably of an APD photodiode array 5 having an upstream array of LSO crystals 4 and an electric amplifier circuit (AMP) 6. However, embodiments of the invention are not limited to the PET detection units 3 having the APD photodiode array 5 and upstream array of LSO crystals 4, and similar or different types of photodiodes, crystals, and devices can be used instead for detecting.

The image processing for representing MR and PET images in mutually superimposed form is performed by a computer 7.

Along its longitudinal direction z the MR tube 2 defines a cylindrical, first visual field. Along the longitudinal direction z the plurality of PET detection units 3 define a cylindrical, second visual field. According to an embodiment of the invention, the second visual field of the PET detection units 3 substantially coincides with the first visual field of the MR tube 2. This is realized by appropriately matching the arrangement density of the PET detection units 3 along the longitudinal direction z.

Figure 2:
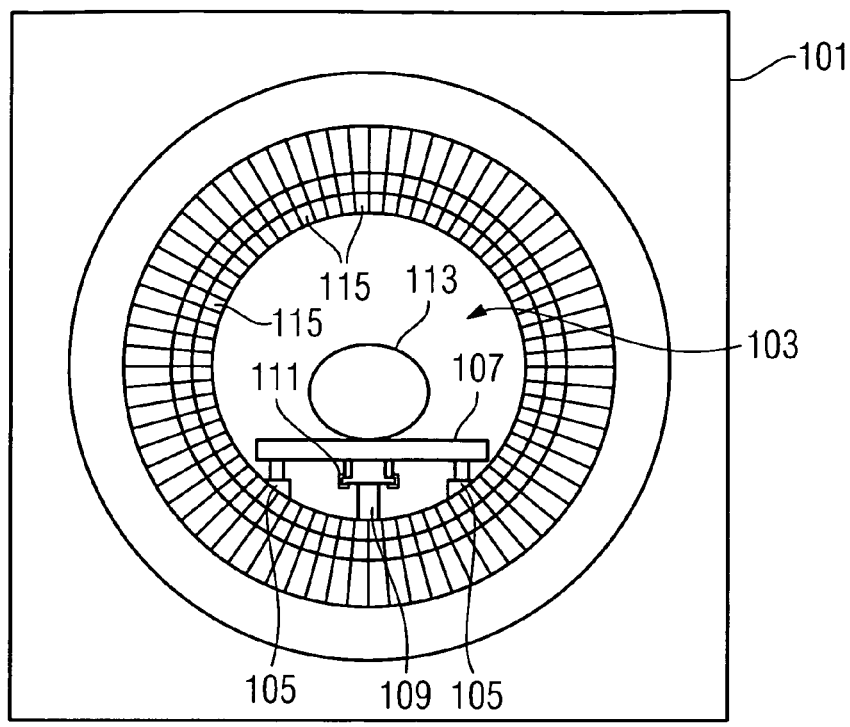
FIG. 2 shows an embodiment of an MR/PET device with a PET phantom.

Shown schematically in FIG. 2 is an MR/PET system 101 that is similar in structure to the MR/PET system shown in FIG. 1. Located inside a patient opening 103 are two running rails 105 on which a patient positioning table 107 is movably mounted. The direction of motion is in this case perpendicular to the drawing plane. Also arranged in the patient opening 103 is a drive unit 109 via which the patient positioning table 107 can be moved. The drive unit 109 engages into a pickup 111 arranged beneath the patient positioning table 107. Force is transmitted via the pickup 111 to the patient positioning table 107 so that the latter can be moved. Disposed on the patient positioning table 107 is a homogeneous PET phantom 113. The gamma quanta arising therein strike the surrounding PET detection units 115 and are detected there. On their way to the upper region of the MR/PET system 101 the gamma quanta are scarcely attenuated because they only have to pass through air on their way from the PET phantom 113 to the PET detection units 115. In the lower region of the MR/PET system 101 the gamma quanta will, though, be attenuated on their way from the PET phantom 113 to the PET detection units 115 by the patient positioning table 107, the running rails 105, and the drive unit 109.

With the aid of the arrangement shown in FIG. 2 it is possible to record a PET data set and use it for calibrating the position of the patient positioning table 107. A suitably matched attenuation map can be ascertained.

Figure 3:
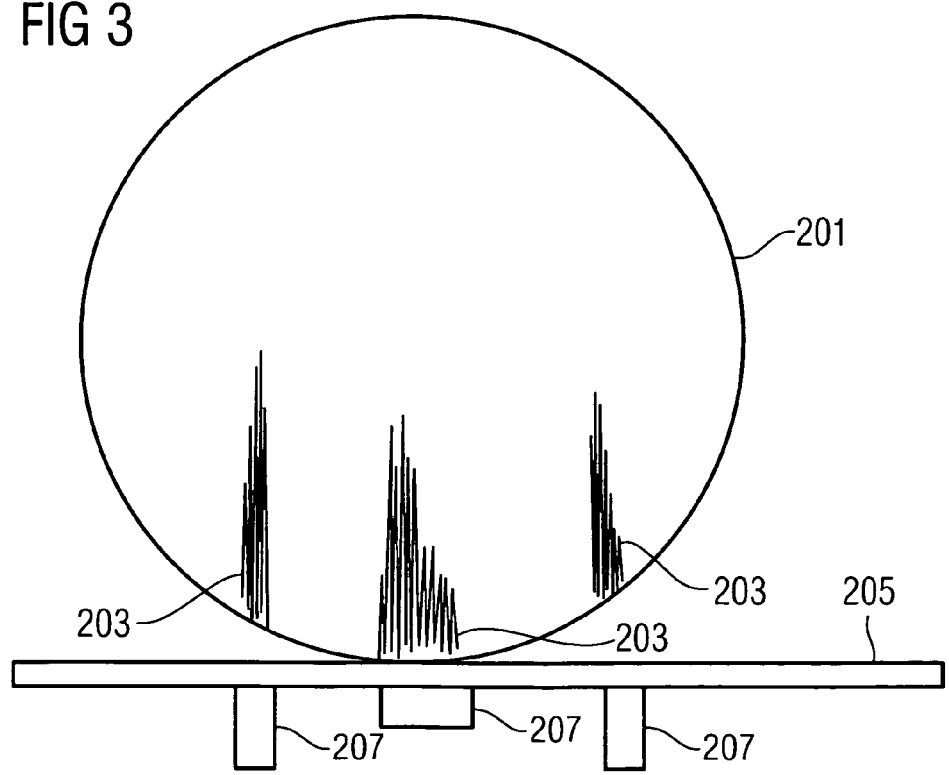
FIG. 3 is a schematic PET image.

Shown in FIG. 3 is a schematic of a PET image 201 of the structure shown in FIG. 2. No attenuation correction was performed in the reconstruction of the PET image 201 so that regions 203 of reduced intensity occur. For better clarification of the causes of the occurrence of the regions 203 of reduced intensity, a patient positioning table 205 is shown that has support structures 207. The regions 203 are caused by the support structures 207 belonging to the patient positioning table 205 and the resulting attenuation of the gamma quanta. The position of the patient positioning table 205 can be ascertained from the location of the regions 203 in the examination volume.

Shown schematically juxtaposed in FIG. 4 are two embodiment variants of the invention. Shown schematically in the lower part of FIG. 4 is a patient positioning table 301 that has two extensions 303. The extensions 303 serve, for example, to mount the patient positioning table 301 movably on corresponding running rails. An in this case rectangular PET phantom 305 is also disposed above the patient positioning table.

Shown in the upper part of FIG. 4 are two charts 307 and 309 in which are plotted, on the horizontal axis 311 and 313 respectively, the site and, on the vertical axis 315 and 317 respectively, the intensity. Shown in the chart 307 is an intensity curve 319 of a PET measurement of the PET phantom 305, which curve has been reconstructed with no attenuation correction. The intensity is largely constant. Only at the positions of the extensions 303 of the patient positioning table 301 do minima 321 occur in the intensity curve 319 that reflect the structure of the patient positioning table 301. A basic map 323 containing attenuation values of the patient positioning table 301 has already been produced from a previous PET transmission measurement or CT measurement. The basic map 323 shows attenuation coefficients and for better clarity is shown in the chart 307. Occurring in the basic map 323 are minima 325 whose location does not, though, coincide with the actual position of the minima 321 of the intensity curve 319. This results from a non-coincident positioning of the patient positioning table 301 compared with the measurement for determining the attenuation values given in the basic map 323. The absolute position of the patient positioning table 301 can be determined from the location of the minima 321 compared with an examination volume of the MR/PET system employed and the basic map 323, and thus the previously ascertained basic map 323 can be corrected in terms of its positions and thus a definitive attenuation map can be produced for the present MR/PET system.

Shown in the chart 309 is an alternative embodiment of the invention. In this example embodiment an intensity curve 331 has been produced using the basic map 323, whose curve is shown also in the chart 309. Because the positions of the occurring minima 325 in the basic map 323 do not coincide with the positions of the extensions 303 of the patient positioning table 301, the attenuation values will in part not be taken correctly into account. Position artifacts 333' and 333" will consequently occur in the intensity curve 331. The position artifacts 333' result from an excessive intensity attenuation caused by the extensions 303 which, owing to shifting of the basic map 323, has not been compensated. This is comparable with the situation in the chart 307 where the attenuation of the extensions 303 resulted in the minima 321.

The position artifacts 333" are due to an overcompensation of lesser attenuation by the patient positioning table 301. The patient positioning table 301 has no extensions at the corresponding positions. However, the erroneous position of the basic map 323 causes those regions to overlap the minima 325 in the basic map 323. A maximum is consequently in each case produced in the intensity curve 321 as the position artifact 333". If the intensity curve 331 is examined for the occurrence of such type of position artifacts 333' and 333", then, taking the basic map 323 into account, inferences can be made about the erroneous positioning of the basic map 323 compared with the patient positioning table 301. In the present example the basic map would need to be shifted to the left to be able to take account of the actual position of the patient positioning table 301. In an iterative process the basic map 323 can be shifted and a new intensity curve of the patient positioning table 301 reconstructed. The new intensity curve will then be examined again for position artifacts 333' and 333". The correct position of the patient positioning table 301 and hence of the basic map 323 will have been found when no more position artifacts 333' and 333" occur after an intensity curve has been reconstructed and the intensity curve is homogeneous. A definitive attenuation map for the patient positioning table 301 can then be produced analogously to the previous example embodiment.

The embodiments of the invention explained using the patient positioning table as an example can be applied also to other components permanently connected to the MR/PET such as a head coil or neck coil.

In an alternative embodiment variant of the invention a 3D scanner is arranged inside or outside the patient opening. It is possible by means of said 3D scanner to register the positions of the patient positioning table and of other accessory parts such as, for example, a head coil or local coils and adjust corresponding attenuation maps in realtime. For registering the positions it is possible to employ specific marking elements that enable the respective position to be established by the 3D scanner but are not visible in MR and PET images.

It is alternatively possible, analogously to known methods (see DE 10 2005 013 851 A1, the entire contents of which are hereby incorporated herein by reference), to furnish the components with marking elements that will be visible on MR images. These can be marking elements that have an explicit shape, for example crosses, triangles or rectangles, and are filled with, for instance, water. Spherical marking elements are likewise possible. Here, too, the attenuation map of the respective component can be matched to the component's actual position through position determination on the MR images.

The patent claims filed with the application are formulation proposals without prejudice for obtaining more extensive patent protection. The applicant reserves the right to claim even further combinations of features previously disclosed The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing an attenuation map for a component of an MR/PET system, comprising:
   ascertaining attenuation values of the component;
   producing a basic map from the ascertained attenuation values;
   ascertaining a position of the component relative to an examination volume of the MR/PET system; and
   producing the attenuation map by correcting the basic map using the ascertained position.

2. The method as claimed in claim 1, wherein the component has marking elements embodied as able to emit a magnetic resonance signal after being excited and wherein the component's position is ascertained by recording an MR image and evaluating image data contained about the markings.

3. The method as claimed in claim 1, wherein ascertaining the component's position comprises:
   combining the component with a homogeneous MR phantom;
   recording an MR data set of the MR phantom; and
   evaluating the recorded MR data set in terms of the component's position compared with the examination volume.

4. The method as claimed in claim 1, wherein the MR/PET system includes an optical registration system and wherein the component's position is ascertained by registering it via the registration system, the component having a marking element embodied such that the component is registerable by the optical registration system.

5. The method as claimed in claim 1, wherein ascertaining the of the component's position comprises:
   combining the component with a homogeneous PET phantom;
   measuring a PET data set of the PET phantom;
   reconstructing a PET image from the measured PET data set; and
   evaluating the reconstructed PET image in terms of the component's position compared with the examination volume.

6. The method as claimed in claim 5, wherein the PET image is reconstructed without taking attenuation values into account and the evaluation of the PET image comprises:
   ascertaining location-dependent intensity modulations in the PET image;
   evaluating the location of the intensity modulations in terms of the location of the examination volume; and
   establishing the component's position using the evaluated location of the intensity modulations.

7. The method as claimed in claim 5, wherein the PET image is reconstructed using the basic map and a predefined position of the component, and wherein the evaluation of the PET image comprises:
   examining the PET image for position artifacts;
   correcting the component's position taking identified position artifacts into account;
   reconstructing another PET image using the basic map at the component's corrected position; and
   iterating the last three method-specific steps until no more position artifacts can be detected.

8. A non-transitory computer readable medium including program segments for, when executed on a computer device, causing the computer device to implement the method of claim 1.

9. A system for producing an attenuation map for a component of an MR/PET system, comprising:
   means for ascertaining attenuation values of the component;
   means for producing a basic map from the ascertained attenuation values;
   means for ascertaining a position of the component relative to an examination volume of the MR/PET system; and
   means for producing the attenuation map by correcting the basic map using the ascertained position.

10. The system as claimed in claim 9, wherein the component has marking elements embodied as able to emit a magnetic resonance signal after being excited and wherein the component's position is ascertained by recording an MR image and evaluating image data contained about the markings.

* * * * *